United States Patent [19]

Hussmann et al.

[11] Patent Number: 4,740,647
[45] Date of Patent: Apr. 26, 1988

[54] CYCLIZATION CATALYST

[75] Inventors: Gregory P. Hussmann, Warrenville; Patrick E. McMahon, Wheaton, both of Ill.

[73] Assignee: Amoco Corporation, Chicago, Ill.

[21] Appl. No.: 925,326

[22] Filed: Oct. 31, 1986

[51] Int. Cl.$^4$ .............................................. C07C 12/00
[52] U.S. Cl. .................................... 585/411; 585/417; 585/418
[58] Field of Search ........................ 585/411, 417, 418

[56] References Cited

U.S. PATENT DOCUMENTS 4,024,171  5/1977  McArthur ............................ 585/419

Primary Examiner—Curtis R. Davis

Attorney, Agent, or Firm—Matthew R. Hooper; William H. Magidson; Ralph C. Medhurst

[57] ABSTRACT

Cyclization of aliphatic moieties of 3–20 carbons which comprises contacting a suitable starting compound comprising the aliphatic moiety with a catalyst comprising at least one member selected from the group consisting of copper aluminum borate and zero valent copper on a support comprising aluminum borate under appropriate reaction conditions to obtain a compound having at least one more cyclic moiety than the starting compound. Preferably, the aromatic which undergoes cyclization is an alkenyl group attached to an aromatic nucleus. The present invention can be used to dehydrocyclize alkenylbenzenes to alkylnaphthalenes. In particular, 5-(o-tolyl)pentene can be dehydrocyclized to mixtures of 1,5-, 1,6-, and 2,6-dimethylnaphthalene.

14 Claims, No Drawings

CYCLIZATION CATALYST

The present invention relates generally to processes for cyclization of aliphatic moieties to afford compounds having at least one more ring moiety than the starting compound. More particularly, the invention is directed to a process for converting aliphatic moieties of 3-20 carbons to cyclic moieties which comprises contacting a suitable starting compound comprising said aliphatic moiety with a catalyst comprising at least one member selected from the group consisting of copper aluminum borate and zero valent copper on a support comprising aluminum borate under appropriate reaction conditions to obtain a compound having at least one more cyclic moiety than the starting compound, provided (a) if the starting compound comprises said aliphatic moiety bonded to an aromatic nucleus, the aliphatic moiety shall include a straight chain of at least two carbons extending from the aliphatic carbon to which the aromatic nucleus is bonded; and (b) if the starting compound is aliphatic, the compound shall include a straight chain of at least five carbons. Preferably, the aliphatic moiety which undergoes cyclization is an alkenyl group of 3-20 carbons attached to an aromatic nucleus. In a preferred embodiment of the invention, the catalyst achieves dehydrocyclization, i.e., simultaneous cyclization and dehydrogenation of alkenylbenzenes to afford alkylnapthalenes. The present invention is useful for dehydrocyclization of 5-(o-tolyl)-pentene to afford a mixture comprising 1,5-, 1,6- and 2,6-dimethylnapthalene.

Alkylnapthalenes, in particular dimethylnaphthalenes, are valuable chemical intermediates which can be oxidized to naphthalenedicarboxylic acids as described for example in Duling U.S. Pat. No. 3,293,223, Yamashita et al. U.S. Pat. No. 3,870,754, and Wynkoop U.S. Pat. No. 3,274,241. These patents disclose the utility of naphthalenedicarboxylic acids as intermediates leading to various industrial chemicals, polyesters, dyestuffs, and the like.

The diacid, 2,6-naphthalenedicarboxylic acid is an especially valuable starting material for preparing polyesters which have superior physical and chemical properties. For example, the polyester obtained from reaction of 2,6-naphthalenedicarboxylic acid and ethylene glycol (polyethylene napthalene-2,6-dicarboxylate) has a glass transition temperarure (Tg) in the range of 150° to ~180° C. Because the Tg of the polyester is above the boiling point of water, textiles fabricated from fibers of this polyester are ideal wash and wear materials as they neither gain nor lose creases during laundering in hot water and can be dried at relatively high temperatures without danger of melting. See e.g. U.S. Pat. No. 3,123,587. Unfortunately 2,6-dimethylnaphthalene is not available at a price which would render its oxidation to the 2,6-diacid commercially attractive.

Several methods of preparing 2,6-dimethylnapthalene from either synthetic or natural sources have been proposed. For example, the compound occurs in coal tar and in cracked petroleum distillate, but is present only in low proportions along with other dimethylnaphthalene isomers and other hydrocarbon compounds. Separation of the desired 2,6-dimethylnaphthalene from such a mixture in high purity is economically prohibitive. From a synthetic standpoint, the selective preparation of specific disubstituted naphthalene isomers is difficult if naphthalene is used as the starting material because most naphthalene ring substitution reactions have poor selectivity and give a mixture of disubstituted isomers which are difficult to separate.

Another and potentially attractive synthesis of 2,6-dimethylnaphthalene from relatively abundant starting materials (i.e., xylene and butadiene) was disclosed in the art about 20 years ago, shortly after several researchers proposed that the ten dimethylnaphthalene isomers could be categorized into the following three groups or "triads" based upon their relative ease of isomerization:

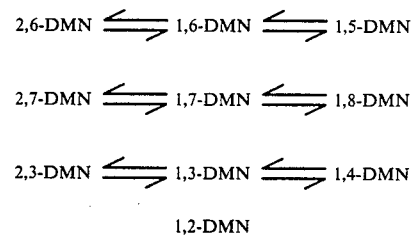

1,2-DMN

See G. Suld et al., *J. Org. Chem.*, 29:2939-2946 (1964) and Suld U.S. Pat. No. 3,109,036. These references disclose that acid catalyzed isomerization within a triad readily occurs, while isomerization between triads is difficult. Thus 1,5 DMN is readily isomerized by means of acid catalysis to the 1,6 and 2,6 isomers, but no others.

Following discovery that 1,5-DMN is readily isomerizable to 2,6-DMN, Eberhardt U.S. Pat. No. 3,244,758 disclosed a three-step process for preparing 1,5-DMN which could be summarized as follows:

(1) catalytic carbanionic addition of butadiene to o-xylene to yield 5-(o-tolyl)-2-pentene;
(2) cyclization of 5-(o-tolyl)-2-pentene to 1,5-dimethyltetralin; and
(3) dehydrogenation of 1,5-dimethyltetralin to 1,5-dimethylnaphthalene.

The above three steps, plus a fourth step involving isomerization of 1,5 DMN to afford 2,6 DMN have spurred numerous patents over the past twenty years claiming improvements in one or more of the steps. For example, the U.S. patents listed below are directed primarily to step (1) above described broadly as the reaction of alkylbenzenes with conjugated dienes to produce alkenylbenzenes:

U.S. Pat. No. 3,766,288
U.S. Pat. No. 3,865,889
U.S. Pat. No. 3,904,702
U.S. Pat. No. 3,953,535
U.S. Pat. No. 3,954,896
U.S. Pat. No. 4,018,840

The following U.S. Patents are directed to steps (2) and (3), i.e., cyclization of the alkenylbenzene (from step one, above), followed by dehydrogenation to produce the corresponding naphthalenes:

U.S. Pat. No. 3,781,375
U.S. Pat. No. 3,843,737
U.S. Pat. No. 3,997,616

Patents directed to the final step of isomerizing 1,5-DMN to 2,6-DMN, include the following:

U.S. Pat. No. 3,775,496
U.S. Pat. No. 3,775,498
U.S. Pat. No. 3,798,280
U.S. Pat. No. 3,957,896

While the above four-step process for preparing 2,6-DMN from o-xylene and butadiene has received considerable attention, it is still too costly to be commercially feasible. Efforts to improve the economics of the process have included attempts to combine one or more of the four steps in a single reaction. Of particular interest in this regard are catalysts capable of simultaneously cyclizing 5-(o-tolyl)pentene and dehydrogenating the resulting dimethyltetralin to 2,6-DMN.

While Satek U.S. Pat. No. 4,590,324 discloses dehydrogenation of alkylaromatics containing at least two carbons in at least one alkyl group to alkenylaromatics using a catalyst comprising metallic copper on a support comprising aluminum borate, the patent does not disclose or suggest use of the catalyst for cyclization or dehydrocyclization to afford compounds having at least one more aliphatic or aromatic ring than the starting compound.

Dehydrocyclization of alkenylaromatics in a single step is discussed in Eberhardt U.S. Pat. No. 3,244,758. Eberhardt discloses that the combination of cyclization and dehydrogenation to form an additional aromatic ring can be brought about by contacting the alkenylaromatic with a catalyst having both cyclization and dehydrogenation activity such as platinum on alumina or silica alumina.

Given the high cost of platinum, need exists for less expensive catalyst compositions capable of effecting simultaneous ring closure and dehydrogenation in a variety of hydrocarbon compounds.

A general object of the present invention is to provide a process for cyclizing aliphatic moieties of 3–20 carbons to obtain aliphatic or aromatic cyclic moieties having at least one more ring than the original moiety, preferably wherein the catalyst utilized is capable of effecting simultaneous cyclization and dehydrogenation thereby resulting in formation of an aromatic ring group.

A further object of the invention is to provide a dehydrocyclization process for converting alkenylaromatics to aromatic hydrocarbons having at least one more aromatic ring than the starting alkenylaromatic, wherein the process utilizes a catalyst capable of performing the requisite cyclization and dehydrogenation in a single step.

Still a further object of the invention is to provide a cyclization and/or dehydrocyclization process for converting alkenylbenzenes to alkylnaphthalenes.

Still a further object is to provide a cyclization/dehydrocyclization process for converting 5-(o-tolyl)pentene to a mixture comprising 1,5-dimethyltetralin and 1,5-dimethylnaphthalene. Other objects appear hereinafter.

We have now found that the objects of the present invention are provided for in a cyclization process for converting aliphatic moieties of 3–20 carbons to aromatic or aliphatic cyclic moieties which comprises contacting a suitable compound comprising said aliphatic moiety with a catalyst comprising at least one member selected from the group consisting of copper aluminum borate and zero valent copper on a support comprising aluminum borate under appropriate reaction conditions to obtain a compound having at least one more cyclic moiety than the starting compound, provided (a) if the starting compound comprises said aliphatic moiety bonded to an aromatic nucleus, the aliphatic moiety shall include a straight chain of at least two carbons extending from the aliphatic carbon to which the aromatic nucleus is bonded; and (b) if the starting compound is aliphatic, the compound shall include a straight chain of at least five carbons. Preferably, the aliphatic moiety which undergoes cyclization is an alkenyl group of 3–20 carbons attached to an aromatic nucleus. In particular, we have found that copper aluminum borate, zero valent copper on a support comprising aluminum borate, or combinations thereof, act as simultaneous cyclization and dehydrogenation catalysts such that alkenylaromatics wherein the alkenyl group has 3–20 carbon atoms, can be dehydrocyclized to afford aromatic compounds having at least one more aromatic ring than the starting compound. The primary advantage of the cyclization/dehydrocyclization process of the present invention is that alkenylbenzenes can be converted directly to alkylnaphthalenes, without need for carrying out separate cyclization and dehydrogenation steps. In particular, the present invention streamlines the 4-step synthesis of 2,6-dimethylnaphthalene mentioned above by combining cyclization and dehydrogenation of 5-(o-tolyl)pentene to afford 1,5-dimethylnaphthalene.

Copper aluminum borate and finely divided metallic copper on a support comprising aluminum borate are the subject of commonly assigned co-pending applications of Zletz U.S. Ser. Nos. 709,790 and 710,015, now abandoned; of Zletz et al. U.S. Ser. Nos. 710,042 and 711,235, now U.S. Pat. No. 4,645,753; and of Satek U.S. Pat. No. 4,590,324. These applications disclose the preparation, characterization and utility of copper aluminum borate and are hereby incorporated by reference.

As desclosed in Zletz U.S. Ser. No. 709,790, copper aluminum borate ($Cu_{2-X}Al_{6-Y}B_4O_{17}M_mM'_nM''_y$ wherein M is a divalent metal, M' is a monovalent metal, m ranges from 0 to 0.8, n ranges from 0 to 1.6, X ranges from 0 to 0.8 and is equal to the sum of $m+n/2$, M" is a trivalent metal and y ranges from 0 to 1.2) which is at least partially reducible with hydrogen under Temperature Programmed Reduction conditions at a temperature no more than 350° C., preferably having a surface area of at least 5 m² per gram and a pore volume of at least 0.04 cc per gram, is a new catalyst and further that copper aluminum borate can be treated with a reducing agent to form a catalyst comprising finely divided metallic copper (zero valent copper) on a support comprising an aluminum borate. Part of the copper in the copper aluminum borate reacts with a reducing gas at relatively low temperature (about 175° to 350° C.) to form finely divided copper on the aluminum borate support.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, substantially all of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal for example zinc or nickel, copper in the compound is still reducible to metallic copper at relatively low temperature.

While it is not clear at this point whether copper aluminum borate or copper on aluminum borate or combinations of the two is the true catalyst in dehydrogenation reactions and reactions employing a reducing gas, it has generally been found that the induction period for carrying out these reactions is reduced by treating the copper aluminum borate with a reducing agent prior to the desired reaction to produce finely divided metallic copper on an aluminum borate support.

If neat copper aluminum borate having the empirical formula $Cu_2Al_6B_4O_{17}$ is viewed as having the structure $3Al_2O_3 \cdot 2CuO \cdot 2B_2O_3$, the reduction with CO or $H_2$ can be represented in its simplest terms as follows:

$$3Al_2O_3 \cdot 2CuO \cdot 2B_2O_3 + 2H_2 \rightarrow 3Al_2O_3 \cdot 2B_2O_3 + 2Cu + 2H_2O$$

$$3Al_2O_3 \cdot 2CuO \cdot 2B_2O_3 + 2CO \rightarrow 3Al_2O_3 \cdot 2B_2O_3 + 2Cu + 2CO_2$$

X-ray diffraction patterns of the products indicate that the aluminum borate crystal has the formula $2Al_2O_3 \cdot B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table I show the significant lines for unreduced CuAB of this invention, substantially fully reduced CuAB (copper on aluminum borate) of this invention, $Al_4B_2O_9$ and copper.

X-ray data were determined by standard techniques. The radiation was the K-alpha double of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in A, corresponding to the recorded lines, were calculated. In Table I the relative intensities are given in terms of the symbols VVS=very very strong (over 100), VS=very strong (80-100), S=strong (50-80), M=Medium (20-50), W=weak (10-20) and VW=very weak (<10).

TABLE I

| dA | Cu on AB | Cu AB | Uhlig Cu AB | $Al_4B_2O_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |

TABLE I-continued

| dA | Cu on AB | Cu AB | Uhlig Cu AB | $Al_4B_2O_9$ | Cu |
|---|---|---|---|---|---|
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the $Al_4B_2O_9$ and copper.

The significant X-ray diffraction lines for copper aluminum borate are set forth below in Table A.

TABLE A

| dA | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

As disclosed in Satek, part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel and magnesium have been successfully incorporated into copper aluminum borate crystals and, accordingly, X in the above formula can range from about 0.01 to 0.8, preferably about 0.05 to 0.50. Trivalent metal ions can appear as M″ in the above formula, e.g., $Fe^{+++}$. However, chromium forms a chromite and appears to not to replace aluminum.

If desired, non-volatile cations such as alkali metal (M′ in the above formula) or alkaline earth metal cations can be present during the preparation of the copper aluminum borate.

For purposes of this invention the term "aluminum borate" is used in the generic sense to be inclusive of all aluminum borate compounds, such as pure or neat aluminum borate, copper aluminum borate, zinc aluminum borate, etc. "Copper aluminum borate" is used in the generic sense to be inclusive of all compounds containing divalent copper, trivalent aluminum and borate, comprising the X-ray diffraction pattern of $Cu_2Al_6B_4O_{17}$, such as pure or neat copper aluminum borate, copper zinc aluminum borate, aluminum borate/copper aluminum borate, copper aluminum borate/copper chromite, copper aluminum borate/alumina, etc.

Briefly, the copper aluminum borate catalyst or zero valent copper on a support comprising aluminum borate for use in the dehydrocyclization process of the present invention can be prepared either from a gelled precursor in a liquid medium as disclosed in commonly assigned Zletz U.S. Ser. No. 709,790, incorporated herein by reference, or from a dry-mixed precursor as disclosed in U.S. Ser. No. 924,064, incorporated by reference. Regardless of which technique is used, preparation of the catalyst generally involves a three-step procedure comprising: (1) combining a source of divalent copper, trivalent aluminum and boron in the form of the oxide or borate, (2) drying the composition where necessary to remove water or diluent and (3) calcining the composition at a temperature sufficiently high to form crystalline copper aluminum borate having an X-ray diffraction pattern for $CU_2Al_6B_4O_{17}$ as set forth in Table A.

In either the dry or liquid preparation of copper aluminum borate, suitable sources of copper include copper nitrate, copper acetate, copper carbonate, copper borate, basic copper carbonate ($CuCO_2.Cu(OH)_2$), copper acetate monohydrate, copper oxides and copper metal. Copper acetate monohydrate is preferred in the dry preparation. Suitable sources of boron include any solid boron containing reagent. Examples are boric acid, copper borate, aluminum borate, boron oxides, ammonium borate, ammonium hydrogen tetraborate, etc. Suitable sources of aluminum are alumina sols, aluminum nitrate, alumina, aluminum acetate, aluminum borate, etc. These components can be combined in approximately stoichrometric proportions to provide copper aluminum borate having the empirical formula $Cu_2Al_6B_4O_{17}$.

The preparation of copper aluminum borate for use in the present invention can be carried out by the liquid or gel technique described in Zletz. Using this technique, it is generally desirable to combine divalent copper, boron in the form of the oxide or borate ion, and trivalent aluminum in the form of aluminum salts or alumina in an aqueous medium. In order to avoid the introduction of any extraneous ions in the crystalline copper aluminum borate, it is generally desirable to avoid the presence of cations or anions that are not destroyed and/or volatilized during the subsequent drying and/or calcination step. The presence of volatile components in preparation of copper aluminum borate, such as water, $NH_3$, acetate ion, nitrate ion, etc., is advantageous in providing the copper aluminum borate with relatively high surface area and porosity desirable for most catalytic reactions. It is generally preferred to include ammonium salts or ammonium hydroxide in the above aqueous preparation to achieve the desired high surface area and porosity in the final catalyst.

Alternatively, copper aluminum borate catalyst useful in the present invention can be conveniently prepared using a solid-state method as disclosed in De Simone et al. commonly assigned co-pending U.S. Ser. No. 924,064, incorporated herein by reference. The solidstate preparation of De Simone obviates the time-consuming and economically costly step of drying the catalyst precursor prior to calcining.

Briefly, the solid-state preparation of copper aluminum borate comprises (1) dry-mixing powdered reagents comprising suitable precursors of copper oxide (CuO), aluminum oxide ($Al_2O_3$), and boron oxide ($B_2O_3$) with at least about 3 wt % on a dry solids basis of a suitable solid binder to form a superficially dry copper aluminum borate precursor; (2) compacting the dry pre-cursor; and (3) calcining the precursor at a sufficiently high temperature to form crystalline copper aluminum borate. The terms "dry," "dry-mixed," "solid state," "solid," and "superficially dry" are intended to denote conditions, processes, or reagents which are essentially free of liquid materials. These terms are not intended to exclude the presence of ambient atmospheric moisture or the water of hydration in solid reagents. The terms "pre-cursor," "copper aluminum borate precursor," "dry-mixed precursor," etc., denote compositions which, upon calcination at a sufficiently high temperature, result in crystalline copper aluminum borate.

In the dry preparation, the solid reagents comprising suitable precursors of copper aluminum borate should be ground to a powder, individually or as a combination, through a 0.25 mm screen in a high speed grinder. It is important that similar particle sizes of all reagents be attained in order that the solid state reaction to form crystalline copper aluminum borate proceeds as uniformly as possible upon calcination. Following grinding, a superficially dry mixture is prepared by combining the powdered dry reagents with about 3–20 wt % of a suitable solid binder.

A suitable solid binder is one which is capable of holding the powdered reagents together following compaction in a pellet press or extrusion apparatus, and which will burn away upon calcination, thus imparting porosity to the pellet. Preferred binders are solid stearins and the like, graphite, or mixtures thereof. Sterotex, a commercially available vegetable stearin, is particularly well suited as it burns off at a lower temperature than graphite and results in a better catalyst. The preferred amount of binder is at least about 3% by weight of the powdered reagents on a dry solids basis, but up to about 20% may be employed. About 5 wt. percent of the binder is recommended. The binder material can be combined with the powdered reagents using a conventional mixing apparatus for a period of about 10 to about 60 minutes. After the above-prescribed mixing of the powdered reagents and solid binder is completed, the resulting superficially dry mixture can be either extruded or pelletized using conventional techniques and apparatus.

In either the liquid or solid state preparation part of the copper salts or aluminum component can be replaced with divalent and/or trivalent metal salts such as nickel acetate, copper acetate, cobalt acetate, zinc acetate, magnesium nitrate, chromic acetate, ferrous or ferric acetate, etc. Divalent metal ions can appear in the copper aluminum borate as M in the above formula. X-ray diffraction data indicates that zinc, cobalt, nickel, and magnesium have been substantially incorporated into copper aluminum borate crystals and accordingly X in the above formula can range from about 0.01 to 0.8, preferably about 0.05 to 0.50. Trivalent metal ions can appear as M" in the above formula, e.g., $Fe^{+++}$. However, chromium forms a chromite and appears not to replace aluminum. In addition, non-volatile cations such as alkali metal (M' in the above formula) or alkaline earth metal cations can be present during the preparation of the copper aluminum borate.

The catalyst precursor prepared by either of the methods described above should be calcined at a temperature in the range of from about 650° to about 1000°, preferably at least about 800° C. for about 1 to 24 hours, typically in air. The higher the calcination temperature, the shorter the calcination time. Calcinations below about 800° C. tend to provide a catalyst which has low activity for the dehydrocyclization reaction of the present invention. Other things being equal the higher the calcination temperature the lower the surface area and porosity of the copper aluminum borate. Thus, at calcination temperatures exceeding 1000° C. the catalytic activity of the resultant material is substantially diminished. In the present invention the copper aluminum borate precursor mixture (gel preparation) is initially calcined at a temperature of about 200° to 400° C., preferably about 300° C. for 3–4 hours to burn off volatiles, following which the temperature is increased to preferably between 780° and 860° C. for about 3–8 hours. The preferred calcining regime is 820° C. for about 4 hours.

Copper aluminum borate can be treated with any of the metals or metal compounds conventionally used in catalysis. Any one or more of the transition metals or compounds can be utilized such as the metals of Groups IB, IIB, IIIB, IVB, VB, VIB, VIIB and VIII of the Periodic Table. Suitable metals include zinc, cadmium, copper, silver, chrominum, molybdenum, scandium, tungsten, manganese, titanium, rhenium, iron, cobalt, nickel, ruthenium, rhodium, palladium, osmium, iridium, vanadium, platinum, etc. These metals can be present in a concentration of from 0.01 to 30% by weight of the copper aluminum borate catalyst or copper on aluminum borate. These metals or metal compounds can be applied as salts, oxides, etc., and if desired, thermally decomposed to give the corresponding metal or oxides.

If copper aluminum borate is to be used for dehydrocyclization of alkenylaromatics according to the present invention, the catalyst is preferably impregnated or doped with about 0.01 to about 10 wt. % of at least one of the metals selected from the group consisting of platinum, iridium, osmium, palladium, rhodium and ruthenium. Of these, about 0.2 wt. % platinum is preferred for improving the dehydrogenation activity of the catalyst as well as the yield of dimethylnaphthalenes from alkenylbenzenes.

The prescribed amount of metal can be incorporated in the copper aluminum borate using various techniques, for example, by including the metal or metal compound, either as a solid reagent or in solution, directly in the liquid or dry-mixed reagents constituting the pre-calcined copper aluminum borate precursor. It is also feasible to impregnate the calcined copper aluminum borate with a solution comprising the active metal or a salt of the active metal, followed by an additional calcination step.

Preferably, platinum in the range of about 0.01 to 5.0 wt. %, preferably about 2–4 wt. %, is incorporated into the copper aluminum borate catalyst by the latter of the two methods described above, i.e., impregnation of the final calcined catalyst with a solution of the active metal followed by an additional calcination step.

In the present invention, copper aluminum borate and/or zero valent copper on a support comprising aluminum borate prepared in accordance with the procedures outlined above is a cyclization catalyst useful for cyclizing aliphatic moieties of 3–20 carbons to afford compounds having at least one more alicyclic or aromatic ring than the starting compound. In the case of starting compounds in which the aliphatic moiety is bonded to an aromatic nucleus, the aliphatic moiety should have a straight chain of at least two carbons extending from the aliphatic carbon to which the aromatic nucleus is bonded, and if the starting compound is aliphatic, the compound should include a straight chain of at least five carbons.

Among the compounds useful as starting reactants for cyclization/dehydrocyclization according to the present invention are alkenylaromatics comprising an aromatic nucleus (i.e., benzene, naphthalene, etc.) substituted with at least one alkenyl group having 3–20 carbon atoms and wherein the aromatic nucleus has at least one unsubstituted position ortho to the alkenyl group.

Preferred alkenylaromatics for use in the present invention are alkenylbenzenes having the following formula:

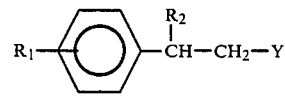

wherein $R_1$ is selected from the group consisting of hydrogen, $C_1$-$C_8$ aliphatic, and —C($R_2$)H—CH$_2$—Y; $R_2$ is selected from the group consisting of hydrogen and $C_1$-$C_{10}$ aliphatic; and Y is selected from the group consisting of —CH=CH—CH$_3$, —CH$_2$—CH=CH$_2$, —CH=CH—CH$_2$—CH$_3$ and —CH$_2$—CH=CH—CH$_3$; provided however the benzene nucleus has at least one unsubstituted position ortho to a ring carbon having said —C($R_2$)H—CH$_2$—Y group attached thereto. The process of the present invention can therefore be used to convert alkenylbenzenes to the corresponding alkylnaphthalenes. In particular 5-(o-tolyl)-pentene can be readily converted in a single dehydrocyclization step to the valuable 1,5-, 1,6-, and 2,6-dimethylnaphthalenes.

Examples of alkenylbenzenes suitable as starting reactants for cyclization/dehydrocyclization over copper aluminum borate according to the present invention include the following: 5-phenyl-2-pentene, 5-(o-tolyl)-2-pentene, 5-(p-tolyl)-2-pentene, 5-(m-tolyl)-2-pentene, 5-phenyl-1-pentene, 5-(o-tolyl)-1-pentene, 5-(p-tolyl)-1-pentene, 5-(m-tolyl)-1-pentene, 5-methyl-5-phenyl-2-pentene, 5-methyl-5-phenyl-1-pentene, 5-methyl-5-(o-ethylphenyl)-2-pentene, 5-methyl-5-(o-ethylphenol)-1-pentene, 5-methyl-5-(p-tolyl)-2-pentene, 6-(o-tolyl)-3-hexene, 6-(o-tolyl)-2-hexene, 6-methyl-6-phenyl-3-hexene, 6-methyl-6-phenyl-2-hexene, and 6-phenyl-3-hexene, and so on.

In the present invention, cyclization of the alkenylaromatic over a catalyst comprising at least one member selected from the group consisting of copper aluminum borate and zero valent copper on a support comprising aluminum borate can effect ring closure (i.e. cyclization) between the alkenyl group and the aromatic nucleus, simultaneously with dehydrogenation, such that the new ring formed is an aromatic. Ring closure occurs at the aromatic carbon atom ortho to the ring carbon atom to which the alkenyl group is attached. If the starting alkenylaromatic has only one alkenyl group, ring closure yields an aromatic containing one more cyclic moiety than the starting alkenylaromatic. If the alkenylaromatic has two alkenyl groups, each group can undergo ring closure with the aromatic nucleus to produce a compound having two more rings than the starting alkenylaromatic. Although we have found that the copper aluminum borate catalyst is capable of effecting simultaneous cyclization and dehydrogenation, selectivity to the dehydrocyclization product (i.e., where the newly formed ring is aromatic) can be substantially less than 100% due to formation of cyclized product which has not undergone dehydrogenation (i.e., where the ring formed is aliphatic).

Dehydrocylization of the alkenylbenzenes enumerated above according to the present invention yields the corresponding naphthalenes, for example: 1-methylnaphthalene from 5-phenyl-2-pentene; 1,5-dimethylnaphthalene from 5-(o-tolyl)-2-pentene; 1,7-dimethylnaphthalene from 5-(p-tolyl)-2-pentene; 1,6- and 1,8 dimethylnaphthalene from 5-(m-tolyl)-2-pentene; 1,4-dimethylnaphthalene from 5-methyl-5-phenyl-2-pentene; 5-methyl-1-ethylnaphthalene from 6-(o-tolyl)-3-hexene, and so on.

The dehydrocyclization process of the present invention can be schematically shown below, using as an example the conversion of 5-(o-tolyl)-2-pentene to 1,5-dimethylnaphthalene:

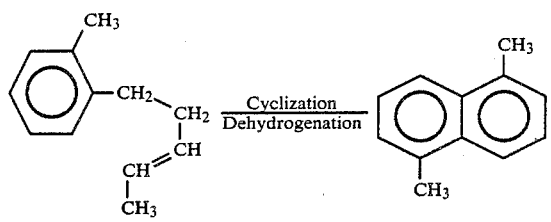

Alkenylaromatics suitable as starting materials for use in the dehydrocyclization process of the present invention can be readily prepared in accordance with conventional methods such as those taught for example in Eberhardt U.S. Pat. No. 3,244,758; Shima et al. U.S. Pat. No. 3,766,288; Mitchell U.S. Pat. No. 3,865,889; and Iwata U.S. Pat. No. 4,018,840, etc. which are hereby incorporated by reference. The synthesis described in these patents generally involves catalytic reaction, in the presence of an alkali metal catalyst, of a conjugated diolefin with an aromatic hydrocarbon having one or more saturated substituent groups which contain benzylic hydrogen to produce the desired alkenylaromatic.

For example, when the conjugated diolefin is butadiene, the reaction thereof with o-xylene in the presence of an alkali metal catalyst yields 5-(o-tolyl)-2-pentene, while m-xylene yields 5-(m-tolyl)-2-pentene and p-xylene yields 5-(p-tolyl)-2-pentene. These products, upon dehydrocyclization with copper aluminum borate, yield respectively 1,5-dimethylnaphthalene, 1,7-dimethylnaphthalene, and a mixture of 1,8- and 1,6-dimethylnaphthalene. When ethylbenzene and butadiene are reacted, the product is 5-phenyl-hexene-2, which upon dehydrocyclization is converted to 1,4-dimethylnaphthalene. If the diolefin is 1,3-pentadiene, reaction thereof with o-xylene in the presence of an alkali metal catalyst yields 6-(o-tolyl)-3-hexene, which, upon dehydrocyclization yields 1-ethyl-5-methylnaphthalene. Reaction of n-propylbenzene with 1,3-pentadiene yields 6-phenyl-3-octene, which dehydrocyclizes to 1,4-diethylnaphthalene. If an alkylnaphthalene such as 1,5-dimethylnaphthalene is reacted with 1,3-butadiene the product, 5-(5-naphthyl)-2-pentene, can be dehydrocyclized to 1,8-penanthrene. If two moles of 1,3-butadiene are reacted with o-xylene, the product 1,2-di-(pentenyl-2)benzene can be dehydrocyclized to 1,8-dimethylphenanthrene. These reactions also yield the corresponding tetralins if the cyclization reaction is not accompanied by dehydrogenation. Thus 5-(o-tolyl)-2-pentene yields 1,5 dimethyltretralin in addition to the naphthalenes.

Thus selected alkylaromatics and diolefins can be reacted in accordance with conventional techniques to produce a variety of alkenyl aromatics which in turn can be cyclized/dehydrocyclized in the presence of copper aluminum borate according to the present invention, to result in specific aromatic compounds having one more ring than the starting alkenylaromatic.

The cyclization/dehydrocyclization process of the present invention is carried out by contacting in a reaction zone a suitable compound having an aliphatic moiety of 3-20 carbons, preferably an alkenylaromatic, with copper aluminum borate under appropriate reaction conditions of temperature, flow rate of reactants (i.e., contact time) and carrier gas selection. The reaction can be conducted anywhere from about 250° C. to about 500° C., preferably about 300°–400° C. Any inert gas such as helium or nitrogen can be used as a carrier gas for the reactants. The reaction can also be run under oxidative conditions by utilizing air as the carrier gas. The carrier gas flow rate and the reactant flow rate should be adjusted such that the contact time of the reactants with the catalyst is about 2 to 15 seconds. Preferably the compound for cyclization should be added to the reaction zone (i.e., catalyst bed) at a WHSV of about 0.5 to 3, and the carrier gas used to sweep the reactant through the reaction zone should be adjusted to a flow rate of about 5 to 15 ml/min.

In addition to its utility for the conversion of alkenylaromatics to naphthalenes or tetralins, the process of the present invention can also be employed in a variety of other cyclization reactions in which an aliphatic moiety of 3-20 carbons is cyclized and/or dehydrocyclized. For example pentane and hexane derivatives can be converted to derivatives of cyclopentane, cyclopentene, cyclohexane and cyclohexene. Longer chain aliphatic compounds can result in cyclic compounds with alkyl side chains. In compounds already having a cyclic or fused polycyclic nucleus, aliphatic side chains attached to these nuclei can be cyclized and/or dehydrocyclized resulting in the addition of a fused or non fused ring to the pre-existing cyclic nucleus. For example, propyl or butyl benzenes or cyclohexanes can be cyclized to the corresponding fused polycyclic compounds including naphthalene and indane. In the case of polycyclic systems comprising one or more fused ring pairs, aliphatic side chains having as few as two carbons can be cyclized to afford an additional fused ring provided the alkyl group is located at a ring carbon adjacent to one of the bridging carbons of the polycyclic nucleus, and ring closure occurs across the bridging carbon. For example, 1-ethylnaphthalene can be converted to acenapthene or acenaphthylene.

EXAMPLE I

Copper aluminum borate catalyst was prepared as follows: 100 grams of boric acid was added to 960 ml of distilled $H_2O$ in a large beaker and dissolved by heating on a hot plate. In a separate beaker, 161.6 grams of copper acetate $(Cu(OAC))_2.H_2O$ was added to 600 ml of moderately heated distilled $H_2O$. After the copper acetate was substantially dissolved (~15 min.), 120 ml of $NH_4OH$ was added to assist dissolution of the copper acetate. Separately, 1,588 grams of PHF alumina sol ($Al_2O_3$) containing about 7.8% solids was poured into a large mixing apparatus, to which was added the hot boric acid solution followed by mixing at a low speed with the top covered for about one minute. To the separate copper acetate solution was added an additional 120 ml of NH₄OH, at which point the copper salt was completely dissolved. The ammonia/copper acetate solution was then added gradually to the mixing apparatus containing the PHF alumina with mixing and stirring as needed. Throughout addition of the ammonia/copper acetate solution to the PHF alumina, hand stirring with a spatula was used to promote even formation of the gel which begins to form immediately upon addition of the copper solution to the alumina. Occasionally, the mixer was turned off in order that material collecting at the bottom of the mixer could be redistributed throughout the mixture. After all the copper solution was added, the gel was mixed at a moderate speed for about 5 minutes, until a smooth consistency was obtained. The gelled precursor was then spread out to dry for 1-2 days under a hood in a layer about 203 mm thick. The air dried catalyst was then collected in crystallizing dishes and placed in a vacuum oven overnight at a temperature of about 45° C. and with a nitrogen purge. Over a period of 2 additional days the vacuum oven temperature was raised gradually (10°-20° C.) until a temperature of 100°-110° C. was reached. The vacuum dried catalyst precursor was then transferred to alumina trays and calcined as follows: 120° to 300° C. gradually over 2 hours; 300° C. for 2 hours; 300° to 820° C. gradually over 3 hours; 820° C. for 3 hours; 820° to 120° C. gradually over 4 or more hours.

EXAMPLE II

Copper aluminum borate containing 2 wt. percent platinum was prepared as follows: to 15.0 grams of copper aluminum borate prepared according to Example I was added with stirring 0.596 gram of tetraamine platinum II nitrate (Pt(NH₃)₄(NO₂)₂) dissolved in 6.93 grams of H₂O. The resulting mixture was dried at 110° C. overnight and calcined at 500° C. for 12 hours.

EXAMPLE III

Copper aluminum borate containing 3 wt. percent platinum (0.819 g of Pt(NH₃)₄(NO₂)₂) was prepared in accordance with the technique described in Example II.

EXAMPLE IV

Copper aluminum borate containing 2 wt. percent palladium was prepared according to the technique of Example II, except that tetraamine palladium nitrate Pd(NH₃)₄(NO₄(NO₃)₂ (II) (0.841 g) was substituted for the platinum salt.

EXAMPLE V

The copper aluminum borate catalyst prepared in accordance with Examples I-IV was tested in five separate runs for cyclization/dehydrocyclization of 5-(o-tolyl)-2-pentene to a mixture of products comprising 1,5-dimethyltetralin, 1,5-dimethylnaphthalene, 1,6-dimethylnaphthalene, and 2,6-dimethylnaphthalene, as follows: a gas phase quartz tube minireactor was charged with approximately 5 ml of copper aluminum borate (or copper aluminum borate impregnated with platinum or palladium). The quartz reactor tube was then heated in a 12" Lindberg furnace to 350° to 400° C. A solution of 5-(o-tolyl)pentene containing both the cis and trans isomer was added to the reactor at a WHSV of 1.1. A 10 ml/min. flow rate of N₂ was used to sweep the reactant through the catalyst bed. The reactor effluent was collected in an ice-cooled receiving flask and analyzed by gas chromatography. The results of five separate runs are as follows:

| | DEHYDROCYCLIZATION OF 5-OTP | | | | |
|---|---|---|---|---|---|
| | | % GC Area | | | |
| | Temp | | | DMN | |
| Catalyst | °C. | 5-OTP | 1,5-DMT | 1,5 | 1,6 | 2,6 |
| CuAlB (I) | 400 | <1 | 31.9 | 4.0 | 10.3 | 6.5 |
| CuAlB (I) | 350 | <1 | 59.2 | 10.8 | 7.0 | 1.1 |
| 2% Pt/CuAlB (II) | 350 | 1.7 | 47.0 | 33.4 | 6.0 | — |
| 3% Pt/CuAlB (IV) | 350 | <1 | 34.7 | 41.2 | 4.0 | — |
| 2% Pd/CuAlB (IV) | 350 | 1.5 | 52.6 | 26.0 | 7.0 | — |

As can be seen from the above data, impregnation increases the yield of 1,5-DMN. However, copper aluminum borate, when not impregnated results in some production of 2,6-dimethylnaphthalene. Thus, to some extent, the copper aluminum borate is not only capable of combining the cyclization and dehydrogenation step in the 3-step process for preparing 1,5-DMN taught in Eberhardt, U.S. Pat. No. 3,244,758, but it further shows activity for isomerization of 1,5-DMN to the desired 2,6-DMN. Conventional techniques for isomerizing 1,5-DMN to 2,6-DMN may be used in conjunction with the present invention to produce the desired 2,6-isomer.

What is claimed is:

1. A cyclization process for converting aliphatic moieties of 3-20 carbons to cyclic moieties which comprises: contacting a compound comprising said aliphatic moiety with a catalyst comprising crystalline copper aluminum borate having the significant x-ray diffraction lines set forth in Table A under appropriate reaction conditions to obtain a compound having at least one more cyclic moiety than the starting compound, provided (a) if the starting compound comprises said aliphatic moiety bonded to an aromatic nucleus, the aliphatic moiety shall include a straight chain of at least two carbons extending from the aliphatic carbon to which the aromatic nucleus is bonded, and (b) if the starting compound is aliphatic, the compound shall include a straight chain of at least five carbons.

2. The process of claim 1 wherein the cyclic moiety formed is aliphatic.

3. The process of claim 1 wherein the cyclic moiety formed is aromatic.

4. The process of claim 1 wherein the aliphatic moiety which undergoes cyclization is an alkenyl group, said starting compound being an alkenylaromatic comprising an aromatic nucleus having substituted thereon at least one said alkenyl group.

5. The process of claim 4 wherein the aromatic nucleus is benzene.

6. The process of claim 4 wherein the aromatic nucleus is naphthalene.

7. The process of claim 4 wherein the aromatic nucleus is phenanthrene.

8. The process of claim 4 wherein the aromatic nucleus is anthracene

9. The process of claim 5 wherein the alkenylaromatic chosen for cyclization has the following formula:

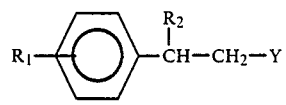

wherein $R_1$ is selected from the group consisting of hydrogen, $C_1$–$C_8$ alkyl and —$C(R_2)H$—$CH_2$—Y; $R_2$ is selected from the group consisting of hydrogen and $C_1$–$C_{10}$ aliphatic, and Y is selected from the group consisting of —CH=CH—$CH_3$, —$CH_2$—CH=$CH_2$, —CH=CH—$CH_2$—$CH_3$ or —$CH_2$—CH=CH—$CH_3$; provided however that the benzene nucleus has at least one unsubstituted position ortho to a ring carbon having said —$C(R_2)H$—$CH_2$—Y group substituted thereon.

10. The process of claim 9 wherein the alkenylaromatic is selected from the group consisting of 5-(o-tolyl)pentene, 5-(m-tolyl)pentene and 5-(p-tolyl)pentene.

11. The process of claim 10 wherein 5-(o-tolyl)pentene is dehydrocyclized to a mixture comprising 1,5-dimethylnaphthalene and 1,6-dimethylnaphthalene.

12. The process of claim 9 wherein the copper aluminum borate contains from about 0.01 to about 10 wt. % of a catalytically active metal.

13. The process of claim 12 wherein the active metal is at least one member selected from the group consisting of platinum, ruthenium, rhodium, palladium, osmium and iridium.

14. The process of claim 13 wherein the active metal is platinum.

* * * * *

UNITED STATES PATENT OFFICE
CERTIFICATE OF CORRECTION

Patent No. 4,740,647          Dated   April 26, 1988

Inventor(s)   Gregory P. Hussman and Patrick E. McMahon

It is certified that error appears in the above-identified patent and that said Letters Patent are hereby corrected as shown below:

| Col. | Line | |
|---|---|---|
| 1  | 48 | "temperarure" and should read --temperature-- |
| 2  | 28 | "1,5 DMN" and should read --1,5-DMN-- |
| 2  | 42 | "1,5 DMN...2,6 DMN" and should read --1,5-DMN...2,6-DMN-- |
| 4  | 32 | "desclosed" and should read --disclosed-- |
| 6  | 49 | "to not to" and should read --not to-- |
| 7  | 30 | "stoichrometric" and should read --stoichiometric-- |
| 7  | 58 | "solidstate" and should read --solid-state-- |
| 11 | 8  | "1,8" and should read --1,8--- |
| 11 | 62 | "1,8-penanthrene." and should read --1,8-phenanthrene-- |

UNITED STATES PATENT OFFICE
CERTIFICATE OF CORRECTION

Patent No. 4,740,647              Dated  April 26, 1988

Inventor(s)  Gregory P. Hussmann and Patrick E. McMahon

It is certified that error appears in the above-identified patent and that said Letters Patent are hereby corrected as shown below:

| Col. | Line | | |
|---|---|---|---|
| 12 | 1 | "1,5 dimethyltretralin" and should be | --1,5-dimethyltetralin-- |
| 13 | 49 | "$(NO_4NO_3)_2$" and should read | --$NO_4(NO_3)_2)$-- |

Signed and Sealed this

First Day of November, 1988

Attest:

DONALD J. QUIGG

Attesting Officer

Commissioner of Patents and Trademarks